(12) United States Patent
Gu et al.

(10) Patent No.: US 11,998,583 B2
(45) Date of Patent: Jun. 4, 2024

(54) FRUCTUS FORSYTHIAE AND RADIX ASTRAGALI COMPOUND PREPARATION, AND PREPARATION METHOD THEREFOR AND USE THEREOF

(71) Applicant: NANTONG UNIVERSITY, Jiangsu (CN)

(72) Inventors: Xiaosong Gu, Jiangsu (CN); Chunkang Tang, Jiangsu (CN); Leilei Gong, Jiangsu (CN); Yu Zhang, Jiangsu (CN); Qiong Cheng, Jiangsu (CN); Xiaoming Yang, Jiangsu (CN); Xiaomin Wang, Jiangsu (CN)

(73) Assignee: NANTONG UNIVERSITY (CN)

( * ) Notice: Subject to any disclaimer, the term of this patent is extended or adjusted under 35 U.S.C. 154(b) by 0 days.

(21) Appl. No.: 17/788,010

(22) PCT Filed: Jul. 14, 2020

(86) PCT No.: PCT/CN2020/101945
§ 371 (c)(1),
(2) Date: Jun. 22, 2022

(87) PCT Pub. No.: WO2021/179505
PCT Pub. Date: Sep. 16, 2021

(65) Prior Publication Data
US 2023/0040479 A1    Feb. 9, 2023

(30) Foreign Application Priority Data
Mar. 12, 2020   (CN) .......................... 202010168799.0

(51) Int. Cl.
| A61K 36/634 | (2006.01) |
| A61K 9/16 | (2006.01) |
| A61K 31/235 | (2006.01) |
| A61K 36/481 | (2006.01) |
| A61P 31/16 | (2006.01) |

(52) U.S. Cl.
CPC .............. *A61K 36/634* (2013.01); *A61K 9/16* (2013.01); *A61K 31/235* (2013.01); *A61K 36/481* (2013.01); *A61P 31/16* (2018.01); *A61K 2236/10* (2013.01); *A61K 2236/331* (2013.01); *A61K 2236/51* (2013.01)

(58) Field of Classification Search
None
See application file for complete search history.

(56) References Cited

FOREIGN PATENT DOCUMENTS

CN           104740370 A   *   7/2015

OTHER PUBLICATIONS

Gu, S., et al., Antitumor, Antiviral, and Anti-Inflammatory Efficacy of Essential Oils from Atractylodes macrocephala Koidz. Produced with Different Processing Methods, Molecules 2019, 24(16), 2956 (Year: 2019).*
Gu, S., et al., Understanding molecular mechanisms of traditional Chinese medicine for the treatment of influenza viruses infection by computational approaches, Mol. Bio Syst., 2013, 9, 2696 (Year: 2013).*
Machine translation of CN-104740370-A Description.*
Machine translation of CN-104740370-A Description (2023).*

* cited by examiner

*Primary Examiner* — H. Sarah Park

(57) ABSTRACT

A Fructus Forsythiae and Radix Astragali compound preparation, and a preparation method therefor and a use thereof is provided. Traditional Chinese medicine formulation components consist of the following raw materials or raw material extracts in parts by mass: 9-11 parts of Flos Lonicerae, 9-11 parts of Fructus Forsythiae, 9-11 parts of Radix Scutellariae, 9-11 parts of Herba Artemisiae Annuae, 9-11 parts of Radix Astragali, 9-11 parts of stir-fried Rhizoma Atractylodis Macrocephalae, 9-11 parts of Herba Pogostemonis, 5-7 parts of Radix Saposhnikoviae, 9-11 parts of Radix Ophiopogonis, and 5-7 parts of Radix Glycyrrhizae. The components can be made into an oral liquid, a granule, a dissolved medicine, or a tablet. Further disclosed is a use of the Fructus Forsythiae and Radix Astragali compound preparation in preparation of medicines for preventing and/or treating a viral influenza disease.

7 Claims, No Drawings

FRUCTUS FORSYTHIAE AND RADIX ASTRAGALI COMPOUND PREPARATION, AND PREPARATION METHOD THEREFOR AND USE THEREOF

FIELD

The present disclosure relates to a Fructus Forsythiae and Radix Astragali compound preparation, and a preparation method therefor and a use thereof, and relates to the technical field of medicines.

BACKGROUND

Influenza (called the flu for short) is a respiratory tract infection mainly caused by influenza viruses, and is high in infectivity and spread rate. The typical clinical symptoms are fever, headache, limb soreness, sneezing, dry throat, sore throat, cough and weakness.

Until now, there has been no specific medicine for treating the influenza clinically, and the flu epidemic endangers social public health safety and health of people. As a result, research and development of a new medicine for viral influenza are in hot demand for modern society and national health.

SUMMARY

In order to solve the deficiencies of the prior art, the present disclosure provides a Fructus Forsythiae and Radix Astragali compound preparation, and a preparation method therefor and a use thereof.

Technical solution: For solving the above technical problem, the technical solutions used in the present disclosure are as follows:

In a first aspect, provided is a Fructus Forsythiae and Radix Astragali compound preparation, including traditional Chinese medicine formulation components. The traditional Chinese medicine formulation components consist of the following raw materials or raw material extracts in parts by mass: 9-11 parts of Flos Lonicerae, 9-11 parts of Fructus Forsythiae, 9-11 parts of Radix Scutellariae, 9-11 parts of Herba Artemisiae Annuae, 9-11 parts of Radix Astragali, 9-11 parts of stir-fried Rhizoma Atractylodis Macrocephalae, 9-11 parts of Herba Pogostemonis, 5-7 parts of Radix Saposhnikoviae, 9-11 parts of Radix Ophiopogonis, and 5-7 parts of Radix Glycyrrhizae.

As a preferred solution, as for the Fructus Forsythiae and Radix Astragali compound preparation, the traditional Chinese medicine formulation components consist of the following components in parts by mass: 10 parts of Flos Lonicerae, 10 parts of Fructus Forsythiae, 10 parts of Radix Scutellariae, 10 parts of Herba Artemisiae Annuae, 10 parts of Radix Astragali, 10 parts of stir-fried Rhizoma Atractylodis Macrocephalae, 10 parts of Herba Pogostemonis, 6 parts of Radix Saposhnikoviae, 10 parts of Radix Ophiopogonis, and 6 parts of Radix Glycyrrhizae.

In some embodiments, the Fructus Forsythiae and Radix Astragali compound preparation includes an effective dose of the traditional Chinese medicine formulation components and a pharmaceutically acceptable excipient.

In some embodiments, dosage forms of the Fructus Forsythiae and Radix Astragali compound preparation include an oral liquid, a granule, a dissolved medicine, and a tablet.

In a second aspect, provided is a preparation method for a Fructus Forsythiae and Radix Astragali oral liquid, including (1) preparing raw materials according to a formulation ratio: 10 parts of Flos Lonicerae, 10 parts of Fructus Forsythiae, 10 parts of Radix Scutellariae, 10 parts of Herba Artemisiae Annuae, 10 parts of Radix Astragali, 10 parts of stir-fried Rhizoma Atractylodis Macrocephalae, 10 parts of Herba Pogostemonis, 6 parts of Radix Saposhnikoviae, 10 parts of Radix Ophiopogonis, and 6 parts of Radix Glycyrrhizae; and washing the medicinal materials with water to remove impurities;
(2) soaking the medicinal materials in deionized water at 25° C. for 120 minutes;
(3) performing water extraction, and performing decocting at 100° C. for 20 minutes;
(4) leaving a decoction to stand at 4° C. for 12 hours, filtering and concentrating the decoction, and adding benzoic acid or sodium benzoate; and
(5) performing potting and sterilizing to obtain a Fructus Forsythiae and Radix Astragali oral liquid.

In a third aspect, provided is a preparation method for a Fructus Forsythiae and Radix Astragali granule, including:
(1) preparing raw materials according to a formulation ratio: 10 parts of Flos Lonicerae, 10 parts of Fructus Forsythiae, 10 parts of Radix Scutellariae, 10 parts of Herba Artemisiae Annuae, 10 parts of Radix Astragali, 10 parts of stir-fried Rhizoma Atractylodis Macrocephalae, 10 parts of Herba Pogostemonis, 6 parts of Radix Saposhnikoviae, 10 parts of Radix Ophiopogonis, and 6 parts of Radix Glycyrrhizae; and washing the medicinal materials with water to remove impurities;
(2) soaking the medicinal materials in deionized water at 25° C. for 120 minutes;
(3) performing water extraction, and performing decocting at 100° C. for 20 minutes;
(4) leaving a decoction to stand at 4° C. for 12 hours, filtering and concentrating the decoction, and adding benzoic acid or sodium benzoate; and
(5) performing drying, granulating, packaging and sterilizing to obtain a Fructus Forsythiae and Radix Astragali granule.

In a fourth aspect, provided is a use of the Fructus Forsythiae and Radix Astragali compound preparation in preparation of medicines for preventing and/or treating a viral influenza disease.

In the formulation, monarch herbs include: Flos Lonicerae, Fructus Forsythiae, Radix Scutellariae, and Herba Artemisiae Annuae; minister herbs include: Radix Astragali, stir-fried Rhizoma Atractylodis Macrocephalae, and Herba Pogostemonis; assistant herbs include: Radix Saposhnikoviae and Radix Ophiopogonis; and an envoy herb is Radix Glycyrrhizae.

The formulation has functions of clearing heat and removing toxic substances, inhibiting virus activity, nourishing yin and relieving cough, benefiting lung and tonifying spleen, strengthening body resistance and eliminating pestilence. The formulation is applicable to influenza, fever, headache, limb soreness, sore throat, cough and asthenia.

Compared with existing traditional Chinese medicines, such as Zhengchaihuyin granule, Banlangen granule, Lianhua Qingwen capsule and Shuanghuanglian oral liquid, beneficial effects of the Fructus Forsythiae and Radix Astragali compound preparation, and the preparation method therefor and the use therefor provided in the present invention are: firstly, pharmaceutical components of the formulation are different from those of the existing related traditional Chinese medicines, and the pharmaceutical composition of the formulation is unique and novel. Secondly, an innovative point of efficacy of the drugs of the formulation lies in that by means of the pharmaceutical composition of the formulation, a strong medicine combined antiviral effect may be generated, and the immune function of the human body is further improved, so as to achieve a desirable integrated synergistic antiviral effect. For example, Flos Lonicerae, Fructus Forsythiae, and Radix Scutellariae all have antiviral effects, and the three traditional Chinese medicines are used in combination in the formulation to enhance the medicine antiviral effect. Moreover, Radix Scutellariae and Radix Glycyrrhizae in the formulation play a better integrated and synergistic antiviral effect by regulating the immune function of the human body, effectively inhibit virus activity, relieve symptoms of a patient, and achieve efficacy of strengthening body resistance and eliminating pathogens. Thirdly, a dialectical theory of the formulation on influenza treatment is unique and innovative, the innovative point is to propose "nourishing yin and relieving cough, benefiting lung and tonifying spleen, strengthening body resistance and eliminating pestilence" based on traditional heat clearing and toxic substance removing. For example, Flos Lonicerae, Fructus Forsythiae, Radix Scutellariae, and Herba Artemisiae Annuae enter lungs, a stomach, a liver, a gallbladder and a large intestine meridian, and have effects of clearing heat and removing toxic substances, clearing lung heat and relieving cough; Radix Astragali, stir-fried Rhizoma Atractylodis Macrocephalae and Herba Pogostemonis have effects of benefiting qi and reinforcing spleen, and enhance resistance of the human body; compatibility of Radix Saposhnikoviae with Radix Astragali and Rhizoma Atractylodis Macrocephalae is Yupingfeng San, and achieves functions of tonifying qi, consolidating superficial resistance, enhancing the immune function of the human body, and strengthening the body resistance. Herba Artemisiae Annuae reduces fever, Herba Pogostemonis eliminates dampness with aromatics, and clears lung-heat and relieves coughing. Radix Ophiopogonis nourishes yin and promotes production of body fluid, nourishes the lung to arrest coughing. Radix Glycyrrhizae invigorates spleen and replenishes qi, clears heat and removes toxic substances, and regulates various drugs to exert a synergistic effect.

DETAILED DESCRIPTION

The present disclosure will be specifically described hereafter in conjunction with embodiments.

Embodiment 1: Preparation of a Fructus Forsythiae and Radix Astragali Oral Liquid Raw materials of a formulation are as follows: 100 parts of Flos Lonicerae, 100 parts of Fructus Forsythiae, 100 parts of Radix Scutellariae, 100 parts of Herba Artemisiae Annuae, 100 parts of Radix Astragali, 100 parts of stir-fried Rhizoma Atractylodis Macrocephalae, 100 parts of Herba Pogostemonis, 60 parts of Radix Saposhnikoviae, 100 parts of Radix Ophiopogonis, and 60 parts of Radix Glycyrrhizae.

Preparation method and steps:
(1) washing medicinal materials with water to remove impurities;
(2) preparing the medicinal materials into 1000 parts by volume and soaking same in deionized water at 25° C. for 120 minutes;
(3) performing water extraction, and performing decocting at 100° C. for 20 minutes;
(4) leaving a decoction to stand at 4° C. for 12 hours, filtering and concentrating the decoction, and adding benzoic acid or sodium benzoate; and
(5) potting and sterilizing to obtain a Fructus Forsythiae and Radix Astragali oral liquid.

Embodiment 2: Preparation of a Fructus Forsythiae and Radix Astragali Granule Raw materials of a formulation are as follows: 100 parts of Flos Lonicerae, 100 parts of Fructus Forsythiae, 100 parts of Radix Scutellariae, 100 parts of Herba Artemisiae Annuae, 100 parts of Radix Astragali, 100 parts of stir-fried Rhizoma Atractylodis Macrocephalae, 100 parts of Herba Pogostemonis, 60 parts of Radix Saposhnikoviae, 100 parts of Radix Ophiopogonis, and 60 parts of Radix Glycyrrhizae.

Preparation method and steps:
(1) washing medicinal materials with water to remove impurities;
(2) preparing the medicinal materials into 1000 parts by volume and soaking same in deionized water at 25° C. for 120 minutes;
(3) performing water extraction, and performing decocting at 100° C. for 20 minutes;
(4) leaving a decoction to stand at 4° C. for 12 hours, filtering and concentrating the decoction, and adding benzoic acid or sodium benzoate; and
(5) drying, granulating, packaging and sterilizing to obtain a Fructus Forsythiae and Radix Astragali granule.

Embodiment 3: Influence of Fructus Forsythiae and Radix Astragali Granule on Lung Lesion in Mice Infected with Influenza Virus Materials: a stock solution (15.6 g crude drug/kg) prepared from Fructus Forsythiae and Radix Astragali granules; ribavirin (positive control, 0.075 g/kg); and chicken embryo, influenza a virus FM1 strain, and ICR mice.

Method: the mice are randomly divided into four groups, each group has six mice, and a normal group, a model group, a ribavirin group, and a Fructus Forsythiae and Radix Astragali granule group are set. The mice are intragastrically administered twice a day, 0.3 ml each time, and the mice in the normal group are administered with double-distilled water at the same dose for five consecutive days. The mice are infected intranasally with virus allantoic droplets, at 15 LD50 challenge doses per mouse. On the sixth day, the mice are killed by cervical dislocation, fixed with a 10% formaldehyde solution, routinely sampled, dehydrated, embedded in paraffin, stained with HE, and read under a light microscope. Depending on different degrees of mild, moderate and severe lesions, the lesions are assigned as 0, 1, 2, 3 and 4 respectively. Lesion scores are computed and statistical analysis is performed. A rank sum test is used, and statistical software SPSS13.0 is used.

Results:
Table Influence of Fructus Forsythiae and Radix Astragali granule on degree of lung lesion in mice infected with influenza virus (n=6)

| Group | Lesion score | | | | |
| --- | --- | --- | --- | --- | --- |
| | Hemorrhage and congestion of lung tissue | Suppurative bronchitis | Bronchitis | Alveolitis | Interstitial pneumonia |
| Normal group | 0 | 0 | 0 | 0 | 0 |
| Model group | 12 | 18 | 15 | 13 | 8 |
| Ribavirin group | 7 | 9 | 3 | 3 | 2 |
| Fructus Forsythiae and Radix Astragali granule group | 3 | 9 | 5 | 6 | 7 |

Note:
(1) In different tissue lesions, differences between the model group, the ribavirin group and the Fructus Forsythiae and Radix Astragali granule group and the normal group have statistical significance ($P < 0.05$).
(2) Differences between the ribavirin group and the Fructus Forsythiae and Radix Astragali granule group have no statistical significance ($P > 0.05$).

The results show that the Fructus Forsythiae and Radix Astragali granule has an effect of reducing the lung lesions of the mice caused by influenza viruses.

Embodiment 4

In general data, from September 2019 to February 2020, patients with clinical influenza who complied with the following symptoms (fever, headache, limb soreness, dry throat, sore throat, cough) are enrolled in the study for oral administration of Fructus Forsythiae and Radix Astragali granule dissolved medicines. Thirty patients, aged 19-60 years, receive one dose of traditional Chinese medicine per day, twice in the morning and evening, for 3-5 consecutive days. Thirty control groups receive open parallel and conventional treatment for control.

Clinical efficacy criteria: in 3 consecutive days of administration, body temperatures return to normal, symptoms of headache, limb soreness, dry throat, sore throat and cough are significantly relieved, and hemogram and chest X-rays are normal. Marked effect and relief are combined into effectivity, and the effective rate is up to 87%.

The present disclosure is recited above in terms of preferred embodiments which are not intended to limit the present disclosure, and all technical solutions obtained by means of equivalent substitution or equivalent transformation fall within the scope of protection of the present disclosure.

What is claimed is:

1. A Fructus Forsythiae and Radix Astragali compound preparation wherein the active agents consist of the following raw material extracts in parts by mass: 9-11 parts of an aqueous extract of Flos Lonicerae, 9-11 parts of an aqueous extract of Fructus Forsythiae, 9-11 parts of an aqueous extract of Radix Scutellariae, 9-11 parts of an aqueous extract of Herba Artemisiae Annuae, 9-11 parts of an aqueous extract of Radix Astragali, 9-11 parts of an aqueous extract of stir-fried Rhizoma Atractylodis Macrocephalae, 9-11 parts of an aqueous extract of Herba Pogostemonis, 5-7 parts of an aqueous extract of Radix Saposhnikoviae, 9-11 parts of an aqueous extract of Radix Ophiopogonis, and 5-7 parts of an aqueous extract of Radix Glycyrrhizae.

2. The Fructus Forsythiae and Radix Astragali compound preparation according to claim 1, wherein,
the compound preparation consists of the following components in parts by mass: 10 parts of an aqueous extract of Flos Lonicerae, 10 parts of an aqueous extract of Fructus Forsythiae, 10 parts of an aqueous extract of Radix Scutellariae, 10 parts of an aqueous extract of Herba Artemisiae Annuae, 10 parts of an aqueous extract of Radix Astragali, 10 parts of an aqueous extract of stir-fried Rhizoma Atractylodis Macrocephalae, 10 parts of an aqueous extract of Herba Pogostemonis, 6 parts of an aqueous extract of Radix Saposhnikoviae, 10 parts of an aqueous extract of Radix Ophiopogonis, and 6 parts of an aqueous extract of Radix Glycyrrhizae.

3. The Fructus Forsythiae and Radix Astragali compound preparation according to claim 1, wherein,
dosage forms of the Fructus Forsythiae and Radix Astragali compound preparation comprise an oral liquid, a granule, a dissolved medicine, and a tablet.

4. A preparation method for a Fructus Forsythiae and Radix Astragali oral liquid, comprising the following steps:
(1) preparing raw materials according to a formulation ratio: 10 parts of Flos Lonicerae, 10 parts of Fructus Forsythiae, 10 parts of Radix Scutellariae, 10 parts of Herba Artemisia Annuae, 10 parts of Radix Astragali, 10 parts of stir-fried Rhizoma Atractylodis Macrocephalae, 10 parts of Herba Pogostemonis, 6 parts of Radix Saposhnikoviae, 10 parts of Radix Ophiopogonis, and 6 parts of Radix Glycyrrhizae; and washing the medicinal materials with water to remove impurities;
(2) soaking the medicinal materials in deionized water at 25° C. for 120 minutes;
(3) performing water extraction, and performing decocting at 100° ° C. for 20 minutes;
(4) leaving a decoction to stand at 4° C. for 12 hours, filtering and concentrating the decoction, and adding benzoic acid or sodium benzoate; and
(5) performing potting and sterilizing to obtain a Fructus Forsythiae and Radix Astragali oral liquid.

5. A preparation method for a Fructus Forsythiae and Radix Astragali granule, comprising the following steps:
(1) preparing raw materials according to a formulation ratio: 10 parts of Flos Lonicerae, 10 parts of Fructus Forsythiae, 10 parts of Radix Scutellariae, 10 parts of Herba Artemisiae Annuae, 10 parts of Radix Astragali, 10 parts of stir-fried Rhizoma Atractylodis Macrocephalae, 10 parts of Herba Pogostemonis, 6 parts of Radix Saposhnikoviae, 10 parts of Radix Ophiopogonis, and 6 parts of Radix Glycyrrhizae; and washing the medicinal materials with water to remove impurities;
(2) soaking the medicinal materials in deionized water at 25° ° C. for 120 minutes;

(3) performing water extraction, and performing decocting at 100° C. for 20 minutes;
(4) leaving a decoction to stand at 4° C. for 12 hours, filtering and concentrating the decoction, and adding benzoic acid or sodium benzoate; and
(5) performing drying, granulating, packaging, and sterilizing to obtain a Fructus Forsythiae and Radix Astragali granule.

6. The Fructus Forsythiae and Radix Astragali compound preparation according to claim 2, comprising an effective dose of the traditional Chinese medicine formulation components and a pharmaceutically acceptable excipient.

7. The Fructus Forsythiae and Radix Astragali compound preparation according to claim 6, wherein,
dosage forms of the Fructus Forsythiae and Radix Astragali compound preparation comprise an oral liquid, a granule, a dissolved medicine, and a tablet.

* * * * *